Figure 1:
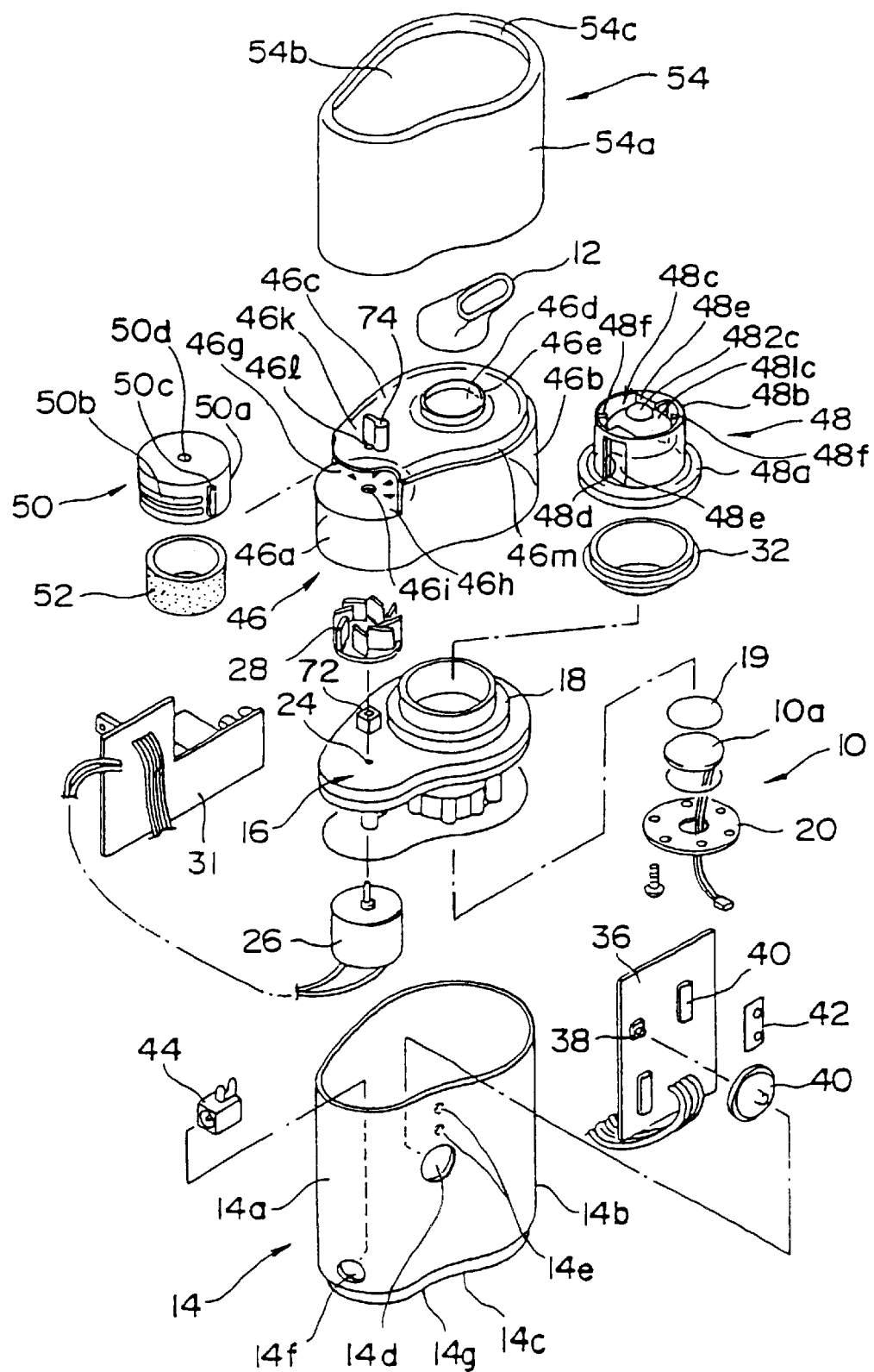
Figure 2:
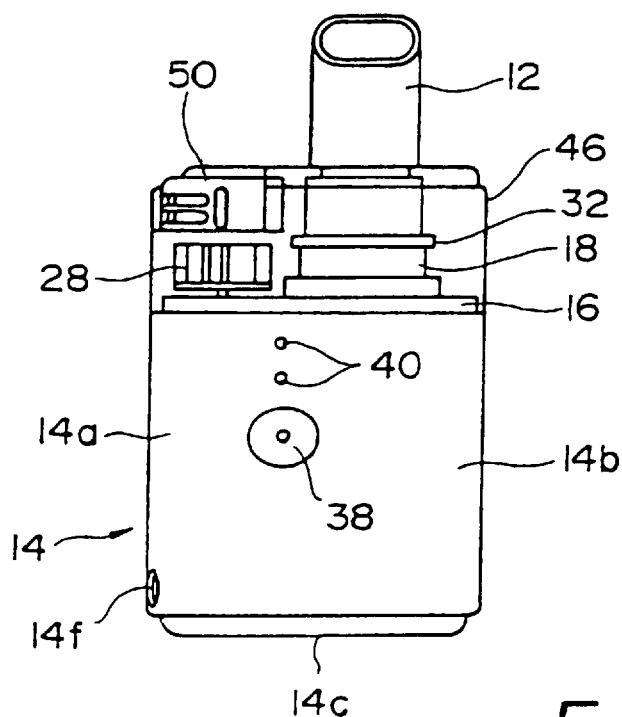

United States Patent
Shibasaki

[11] Patent Number: 5,881,715
[45] Date of Patent: Mar. 16, 1999

[54] HANDY TYPE ATOMIZER

[75] Inventor: Masae Shibasaki, Saitama, Japan

[73] Assignee: A & D Company, Limited, Tokyo, Japan

[21] Appl. No.: 793,096
[22] PCT Filed: Jul. 10, 1995
[86] PCT No.: PCT/JP95/01369
  § 371 Date: Apr. 30, 1997
  § 102(e) Date: Apr. 30, 1997
[87] PCT Pub. No.: WO97/02857
  PCT Pub. Date: Jan. 30, 1997
[51] Int. Cl.[6] .................................................. A61M 11/00
[52] U.S. Cl. .............................. 128/200.14; 128/200.18; 128/203.12
[58] Field of Search ........................ 128/200.14, 200.18, 128/200.21, 200.16, 200.22, 203.12

[56] References Cited

U.S. PATENT DOCUMENTS

| | | | |
|---|---|---|---|
| 1,150,238 | 8/1915 | Winbray | 128/200.21 |
| 1,263,079 | 4/1918 | Leon | 128/200.18 |
| 2,266,705 | 12/1941 | Fox et al. | 128/202.22 |
| 2,906,463 | 9/1959 | Curry | 128/200.21 |
| 4,588,129 | 5/1986 | Shanks | 128/200.18 |
| 4,674,491 | 6/1987 | Brugger et al. | 128/200.18 |
| 4,911,157 | 3/1990 | Miller | 128/200.21 |
| 5,458,135 | 10/1995 | Patton et al. | 128/200.18 |

FOREIGN PATENT DOCUMENTS 3000139  5/1994  Japan .
722747  4/1995  Japan .

Primary Examiner—Aaron J. Lewis
Attorney, Agent, or Firm—Sixbey Friedman Leedom & Ferguson; Thomas W. Cole

[57] ABSTRACT

A rectifying section 48 is disposed between a medicine atomizing means and a nozzle. Said rectifying section 48 has a flange portion 48a fitted to the upper end side of said atomizing means, a guide cylindrical section 48b integrally provided on the inner circumference of said flange portion 48a, a dome section 48c fixed on the inner circumferential face of said guide cylindrical section 48b, and a pair of slit holes 48d installed at the corresponding position of the guide cylindrical section 48b. Said dome section 48c is composed of a largespherical section 481c and a small-spherical section 481b, wherein the large-spherical section 481c is disposed on the center axis of the guide cylindrical section 48b and is formed with a diameter by which the outer circumferential edge thereof is spaced from the inner circumferential face of the guide cylindrical section 48b. The dome section 48c is supported by a pair of stays 48e of which the two points thereof opposite each other extend in the tangential direction, wherein a slit hole 48d is provided there. Furthermore, a pair of wall sections 48f positioned forward of the slit hole 48d are provided between the large-spherical section 481c and the guide cylindrical section 48b in the axial direction of the guide cylindrical section 48b so as to be directed in the diametrical direction of the large-spherical section 481c.

1 Claim, 7 Drawing Sheets

HANDY TYPE ATOMIZER

FIELD OF THE INVENTION

The present invention relates to a handy type atomizer and in particular relates to a technology for improving the convenience in use thereof.

BACKGROUND OF THE INVENTION

An atomizer has been already known as an instrument used for treating the nose and throat, and this kind of atomizer is, for example, utilized for treating primary catarrh, allergic rhinitis, etc. An atomizer used for such a therapy is such that heat or vibration is given to liquefied medicine in order to atomize the same and a patient is caused to inhale the same.

Furthermore, structural examples of these kinds of handy type atomizers are disclosed in, for example, Japanese laid-open utility model publications Nos. 51541 of 1983, 109545 of 1986, 75750 of 1990, etc. Generally, such a kind of atomizer is basically provided with a medicine atomizing means such as a ultrasonic vibrator, a heater, etc., a nozzle for discharging the atomized medicine outside, a feeding means for sending the atomized medicine toward said nozzle, for example, an electric fan.

With an atomizer having such a structure, medicine is usually atomized to be of several microns and is discharged through a nozzle. However, at this time, the following technical themes have been pointed out in the conventional atomizers.

That is, with conventional atomizers including the above-mentioned disclosed in the above publications, they are constructed so that medicine atomized by a medicine atomizing means is discharged outside as it is. However, for example, since the atomized quantity of medicine is very little immediately after commencing the use, the medicine contained in an air flow coming from a feeding means becomes remarkably thin. Generally, these kinds of atomizers are provided with a timer and are constructed so that the same is able to operate during the period of time set by the timer. Therefore, if the timer period is set, including a thin state of medicine, there was a shortcoming where the medicine does not display its effect to the degree expected.

In this case, for example, although it is possible to cause a patient to inhale an appointed liquefied medicine without the inhalation of the atomized medicine commenced immediately after the use of an atomizer but somewhat delayed an appointed duration of time. With such a means, some medicine is uselessly consumed. The present invention was developed in view of solving these shortcomings, and it is therefore an object of the invention to provide an atomizer which is able to uniformly disperse the atomized medicine and effectively cause a patient to inhale the same.

DISCLOSURE OF THE INVENTION

In order to achieve the object, the invention provides an atomizer comprising a medicine atomizing means, a nozzle for discharging the atomized medicine outside, and a feeding means for sending the medicine atomized by said medicine atomizing means toward said nozzle side and further having an atomized medicine rectifying section which is provided between said medicine atomizing means and said nozzle, wherein said rectifying section is characterized in having a guide cylindrical section disposed between said medicine atomizing means and said nozzle with both the ends thereof open, a dome section having a roughly spherical inner face, which is disposed on the center axis of said guide cylindrical section so that the outer circumferential edge of the dome section is spaced from the inner circumferential face of said guide cylindrical section, and a slit hole which introduces an air flow coming from said feeding means from the tangential direction of said dome section into said guide cylindrical section.

According to the atomizer constructed as described above, an atomized medicine rectifying section is provided between the atomizing means and the nozzle, and since the rectifying section has a guide cylindrical section disposed between the atomizing means and the nozzle with both the ends thereof open, a dome section having a roughly spherical inner face, which is disposed on the center axis of said guide cylindrical section so that the outer circumferential edge of the dome section is spaced from the inner circumferential face of said guide cylindrical section, and a slit hole which introduces an air flow coming from said feeding means from the tangential direction of said dome section into said guide cylindrical section, the medicine atomized by said atomizing means is firstly brought into collision with the inner surface of said dome section before being discharged from the nozzle to outside.

At this time, since the inner surface of the dome section is made roughly spherical, the atomized medicine brought into collision with the inner surface thereof is reflected toward the center of the sphere, whereby the same is mixed with the atomized medicine which moves upward. And as the dome section is filled with the atomized medicine, the atomized medicine is caused to flow out, bypassing at the lower end of the dome section, and is guided to the nozzle along with an air flow coming from the feeding means introduced from the tangential direction of the dome section via the slit hole.

BRIEF DESCRIPTION OF THE DRAWINGS

FIG. 1 is a disassembled perspective view showing a preferred embodiment of an atomizer according to the invention, FIG. 2 is an front elevational view of the atomizer shown in FIG. 1 with its cap removed.

FIG. 3 is a longitudinally sectional view of FIG. 2,

FIG. 4 is a perspective view of a rectifying member of the atomizer shown in FIG. 1.

FIG. 5 is a plan view showing the top surface in FIG. 4.

FIG. 6 is a plan view showing the bottom surface in FIG. 5.

FIG. 7 is a longitudinally sectional view in FIG. 5.

FIG. 8 is an enlarged view showing major parts in FIG. 3.

FIG. 9 is a block diagram showing a control circuit of the atomizer shown in FIG. 1.

PREFERRED EMBODIMENT OF THE INVENTION

A detailed description will be given of a preferred embodiment of the invention with reference to the accompanying drawings. FIG. 1 through FIG. 9 show a preferred embodiment of an atomizer according to the invention. In the same drawings, an embodiment in which the invention is applied to a handy type is shown. An atomizer in these drawings has a medicine atomizing means 10, a nozzle 12 for discharging medicine atomized by the atomizing means 10, and a gripping casing 14. Said casing 14 has a small-diametered cylindrical section **14*a***, a large-diametered cylindrical section 14b, and a bottom 14c and is formed so as to have a bottom with the upper end side thereof open and further has a roughly gourd-shaped cross-section which connects the small-diametered cylindrical section 14a with the large-diametered cylindrical section 14b.

Said atomizing means 10 is incorporated at the large-diametered cylindrical section 14b side of the casing 10, and has a piezoelectric vibrator 10a and a vibration liquid 10b. The piezoelectric vibrator 10a is fixed at the lower end of a hollow cylindrical body 18 supported at the cover member 16 which closes the open end of the casing 14 via a protection sheet 19 and an attaching plate 20 so that the lower end of said hollow cylindrical body 18 is closed. The vibration liquid 10b is, for example, distilled water and is sealed in the hollow cylindrical body 18 by adhering a film-like sheet 22 to the intermediate position of the hollow cylindrical body 18, so that the same is brought into contact with the protection sheet 19 secured on the upper surface of the piezoelectric vibrator 10a.

The hollow cylindrical body 18 is fixed at one end (the large-diametered cylindrical section 14b side of the casing 14) of the cover member 16 formed to be roughly gourd-shaped, so that the upper end thereof protrudes upward, and a through-hole 24 is formed at the other end (the small-diametered cylindrical section 14b side of the casing 14) of the cover member 16. The rotating axis of a motor is inserted into this through-hole 24 from below, and an impeller 28 is fitted into the inserted rotating axis from above.

The motor 26 and impeller 28 have diameters which are smaller than the inner diameter of the small-diametered cylindrical section 14a of the casing 14 and they constitute a feeding means which creates an air flow for sending the atomized medicine toward the nozzle 12 side. Power is supplied to the motor 26 via a control circuit mounted on the substrate 31.

Figure 3:
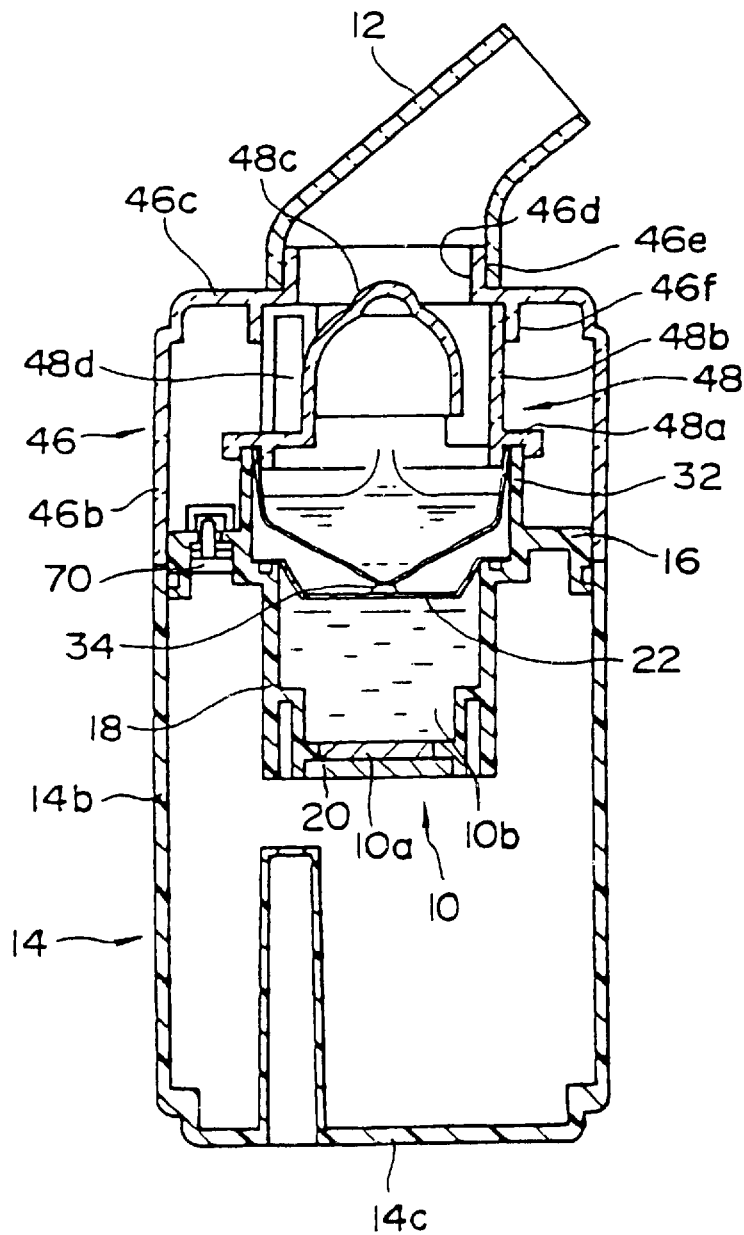
Figure 4:
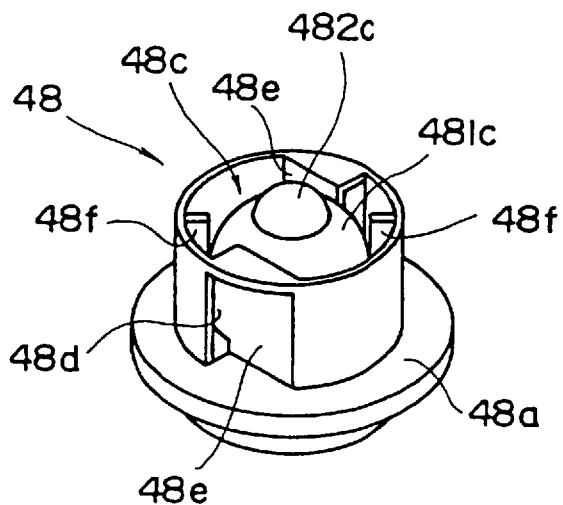
Figure 5:
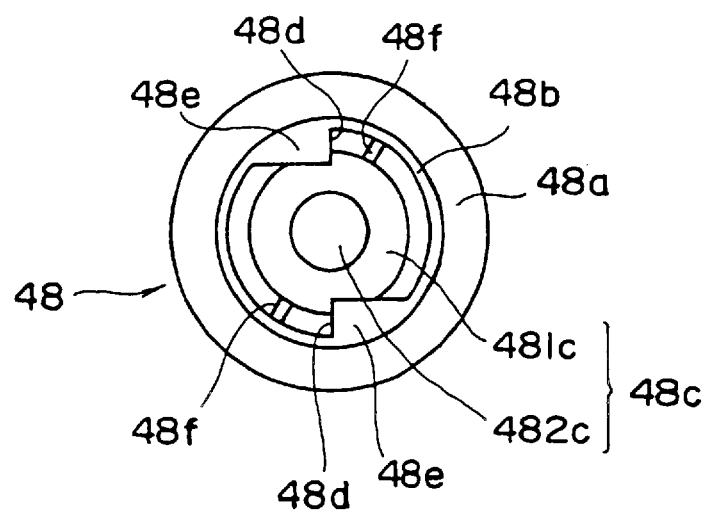
Figure 6:
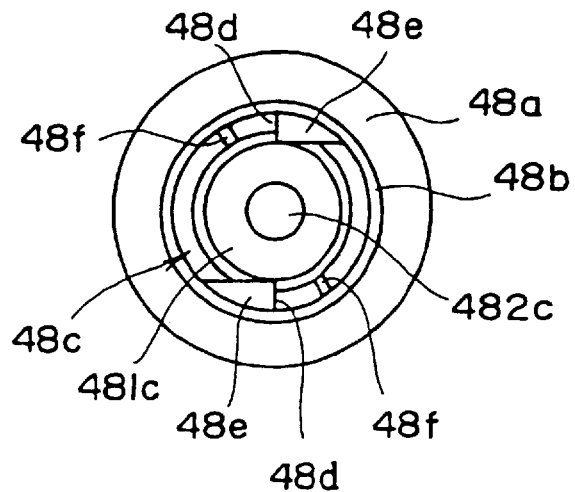
Figure 7:
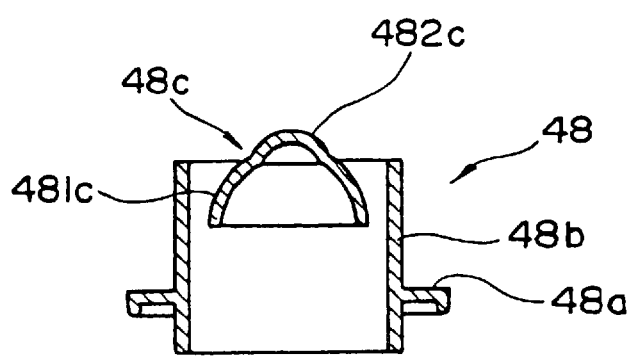

A medicine dish 32 for accommodating medicine is fitted to the inside of the part where the hollow cylindrical body 18 protrudes upward of the cover member 16. A dish 32 according to this preferred embodiment, as concretely shown in FIG. 3, has a bottom inclined downward, wherein a gelled substance 34 intervenes between the bottom and the film-like sheet 22. The gelled substrate 34 is to increase the atomizing efficiency by improving the transmission state of vibrations, and is composed of a polymer, a dampening agent, water, a preserving agent and a surface-active agent, etc.

On the other hand, one large-diametered through-hole 14d is formed at the front side of the gripping case 14, and two small-diametered through-holes 14e are formed at the upper side of the gripping casing 14. Furthermore, one circular through-hole 14f is formed at the side lower end of the small-diametered cylindrical section 14a of the casing 14. An operating switch 38 supported by the substrate 36 inserted into the rear side thereof is inserted into the large-diametered through-hole 14d, and a switch cover 40 is attached to the inserted operating switch 40.

An indication lamp 40 supported at the substrate 40 is disposed at the rear side of the small-diametered through-hole 14e, and this indication lamp 40 is composed of two light emitting diodes, wherein the two light emitting diodes are provided so as to face the small-diametered through-holes 14e via the cover 42. Furthermore, one of the two light emitting diodes blinks corresponding to turning on or off of the operating switch 38, and the other is lit when it is necessary for the secondary battery to be charged.

A connector 44 is attached to the rear side of the circular through-hole 14f, and an adapter 88 to be connected to the commercial power supply is inserted into this connector 44. With the above construction, the operating switch 38 is disposed at the part which connects the small-diametered cylindrical section 14a of the casing 14 with the large-diametered cylindrical section 14b and the indication lamp 40 is provided in the vicinity of this operating switch 38.

The cover member 16 is fitted to and fixed at the upper open end of the casing 14 so that a part of the upper side thereof protrudes therefrom. A transparent cover 46 is detachably attached from above to the protruded part thereof. The cover 46 is composed of a transparent body the lower end of which is open and the cross-section of which is formed to roughly gourd-shaped equivalently to the casing 14, and has a small-diametered circumferential wall section 46a, a large-diametered circumferential wall section 46b respectively having diameters corresponding to the small-diametered cylindrical section 14a of the casing 14 and large-diametered cylindrical section 46b, and a ceiling section 46c.

A circular through-hole 46d which passes through the ceiling section 46c is provided at the ceiling section 46c on the center of the large-diametered circumferential wall section 46b, at the same time a nozzle attaching port 46e protruding upward is provided at the surrounding thereof, and an annular protrusion 46f protruding downward is provided outside the nozzle attaching port 46e.

Furthermore, a semicircular opening part 46g is made at the upper side of the small-diametered circumferential wall section 46a, and a circular ledge 46h which is linked with the inner surface of the small-diametered circumferential wall section 46a is formed at the lower end inner circumferential side of the opening section 46g. And a circular through-hole 46i is caused to pass through and is formed at the center of the ledge 46h, wherein a plurality of slit holes 46j are secured at the outer circumference of this circular through-hole 46i, and an arcuate wall 46k of which the upper end is linked with the ceiling section 46c is formed at the deep side of the ledge 46h. Furthermore, a small-diametered through-hole 46l is secured at the ceiling section 46c corresponding to the center of the circular through-hole 46i.

On the other hand, a rectifying section 48 of atomized medicine is attached from above to the hollow cylindrical body 18. This rectifying member 48 is, as concretely shown in FIG. 4 through FIG. 7, composed of a flange section 48a fitted to the upper end side of the hollow cylindrical body 18, a guide cylindrical section 48b integrally formed at the inner circumference of this flange section 48a with both the ends thereof open, the upper end side of which is fitted to the annular protrusion 46f, a dome section 48c fixed on the inner circumferential face of this guide cylindrical section 48b, and a pair of slit holes 48d secured at the position to which the guide cylindrical section 48b corresponds.

In this preferred embodiment, the dome section 48c consists of a large-spherical part 481c formed to be semi-spherical, and a small-spherical part 482c protruding from the upper end of this large-spherical part 481c. The large-spherical part 481c is disposed on the center axis of the guide cylindrical section 48b, is formed with a diameter with which the outer circumferential edge thereof is spaced from the inner circumferential face of the guide cylindrical section 48b, and is supported by a pair of stays 48e of which the two points opposite each other extend in the tangential direction, at which slit holes 48d are provided.

A pair of wall sections 48f positioned forward of the slit holes 48d are provided between the large-spherical section 481c and the guide cylindrical section 48b along the axial direction of the guide cylindrical section 48b, being directed to the diametrical direction of the large-spherical section 481c. Furthermore, in this preferred embodiment, although the wall sections 48f are provided along the axial direction of the guide cylindrical section 48b, and are opposite the slit holes 48d, for example, the upper side thereof may be inclined in a direction along which the same is spaced from the slit hole 48d. On the other hand, an air flow regulating member 50 is mounted in the opening section 46g. Said air flow regulating member 50 is formed to be cap-like, a filter 52 is disposed at the inner circumferential face of the circumferential wall 50a thereof, and a hole 50b and slide grip 50c which extend in the circumferential direction are provided at the circumferential wall 50a. Furthermore, a small-diametered protrusion 50d protruding upward is secured at the center of the ceiling section. This air flow regulating member 50 is positioned and mounted by fitting the small-diametered protrusion 50d to the small-diametered through-hole 461 of the cover 46, whereby the air flow created by the impeller 28 can be adjusted by changing the length of the part where the hole 50d is exposed to the opening section 46g, by causing the air flow regulating member 50 to move in the circumferential direction via the slide grip 50c.

In this preferred embodiment, the nozzle 12 is composed of a transparent rubber-based member and is attached by fitting the base part side thereof to the nozzle attaching portion 46e of the cover 46. At this time, it is possible to optionally select the discharging direction of the atomized medicine by changing the fitting state of the base part. Still furthermore, in the case of this preferred embodiment, since the nozzle 12 is made of a soft rubber-based member, it is also possible to change the discharging direction by causing the nozzle 12 to rotate in a state where the same is fitted to the nozzle attaching port 46e.

A notched part 46m which is able to be fitted to the cap 54 attached from above the cover 46 is formed at the outer circumferential edge of the ceiling part 4c of the cover 46. The cap 54 has a circumferential wall part 54a of which the cross-section is similar to that of the casing 14, and a ceiling part 54b. A concave part 54c which is able to be fitted to a roughly gourd-shaped convex part 14g secured at the lower end face of the casing 14.

Figure 8:
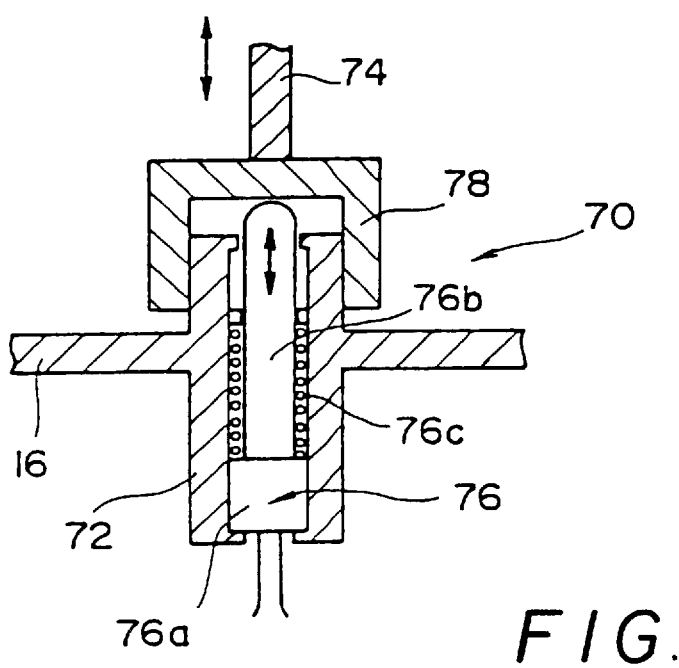

A switch 70 is provided between the gripping casing 14 and the cover 46. Said switch 70 is, as clearly shown in FIG. 8, composed of a switch accommodating section 72 provided at the cover member 16 which closes the upper end opening of the gripping casing 14, a switch operating section 74 formed on the inner circumferential face of the cover 46, and a switch body 76 accommodated in said switch accommodating section 72.

The switch accommodating section 72 is disposed in the vicinity of the part where the small-diametered cylindrical section 14a of the gripping casing 14 is connected to the large-diametered cylindrical part 14b and is formed to be square-tubular with both the ends thereof open. The switch operating section 74 is provided at the switch accommodating section 72 corresponding to the position of the section 72, and a waterproof cover 78 which covers the outer circumference of the switch accommodating section 72 is provided at the lower end of the switch operating section 74. The switch body 76 is composed of a switch mechanism 76a having a pair of always open contacts which are spaced from each other in a constant state, a rod 76b which is interlocked with this switch mechanism, and a spring 76c which always presses the rod 76b upward.

Figure 9:
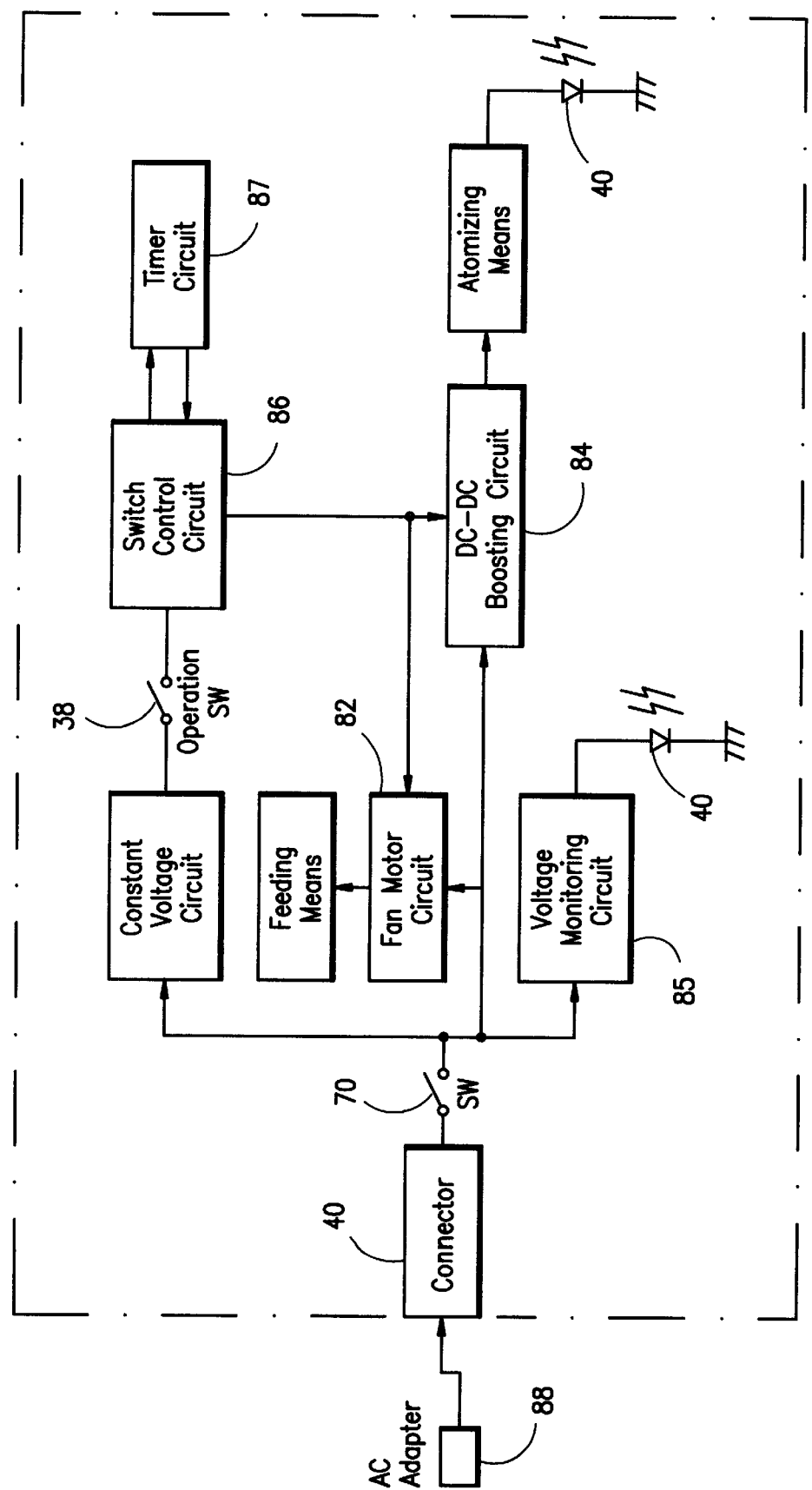

If, with the switch 70 constructed as described above, the rod 76b is pressed down against a pressing force of the spring 76c by the switch operating section 74, the contacts of the switch mechanism section 76 are electrically connected. Furthermore, the switch 70 is not limited to such a mechanical type as described above, for example, an optical type such as a photocoupler may be employed. FIG. 9 is a block diagram of a control circuit mounted in a substrate 31 of the abovementioned atomizer. The control circuit shown in the same drawing has a switch 70 which is connected to the connector 44 in series, a constant voltage circuit 80 which is connected in parallel to the switch 70, a fan motor drive circuit 82, a boosting circuit 84, a voltage monitoring circuit, and a switch control circuit 86 connected to the output side of the constant voltage circuit 80 via the operating switch 38.

A motor 26 of the feeding means is connected to the output side of the fan motor circuit 38. A piezoelectric vibrator 10a and a display 40 are connected to the output side of the boosting circuit 84. The display 40 is connected to the output side of the voltage monitoring circuit 85. A timer circuit 87 which is able to set the operating time of the atomizer is connected to the switch control circuit 86. An appointed direct current voltage is supplied to the connector 44 via an AC adapter 88 in which a secondary battery is incorporated. The switch 70 operates only when the detachable cover 46 is mounted at the gripping casing 14 in order to supply power to the motor of the medicine atomizing means and the feeding means.

Furthermore, with a handy type atomizer constructed as described above, medicine is placed in a medicine dish 32 and the operating switch 38 is turned on, whereby vibrations of the piezoelectric vibrator 10a are transmitted to the medicine via a vibration liquid 10b, the liquefied medicine is atomized, and the atomized medicine is discharged through the nozzle 12 along with an air flow created by the impeller 28.

At this time, with the atomizer according to the preferred embodiment, since a rectifying section 48 for atomized medicine is provided between the atomizing means 10 and the nozzle 12, the actions and effects which will be described in detail are easily obtained. That is, since the rectifying section 48 is equipped with a guide cylindrical section 48*b* disposed between the medicine atomizing means 10 and the nozzle 12 with both the ends thereof open, a dome section 48*c* having a roughly spherical inner face, which is disposed on the center axis in said guide cylindrical section 48*b* so that the outer circumferential edge thereof is spaced from the inner circumferential face of the guide cylindrical section 48*b*, and a slit hole 48*d* for introducing an air flow coming from the feeding means (motor 26, impeller 28) from the tangential direction of the dome section 48*c* into the guide cylindrical section 46*b*, the medicine atomized by the medicine atomizing means is firstly introduced into the guide cylindrical section 48*b* and is brought into collision with the inner face of the dome section 48.

At this time, since the inner face of the dome section 48*c* is formed to be roughly spherical, the atomized medicine brought into collision with the inner face of the dome section is reflected toward to the center of the sphere and is mixed with the atomized medicine which goes up from below. And as the dome section 48*c* is filled with the atomized medicine, the atomized medicine is caused to flow out, bypassing at the lower end of the dome section, and is guided into the nozzle 12 along with an air flow introduced from the tangential direction of the dome section 48*c* via the slit hole 48*d* and coming from the feeding means.

Accordingly, for example, even when the atomized quantity of medicine from the medicine atomizing means 10 is very little immediately after commencing the use, the medicine discharged through the nozzle 12 does not become thin, and it is possible to uniformly disperse the atomized medicine discharged by the nozzle 12. Furthermore, the above preferred embodiment is based on a case where the invention is applied to a handy type atomizer. However, the invention is not limited to this type. For example, it is applicable to an installation type atomizer.

Furthermore, in the above preferred embodiment, although a medicine atomizing means 10 is composed of a piezoelectric vibrator 10*a* and a vibration liquid 10*b*, the invention is not limited to this. For example, the atomizing means 10 may be a heating means such as a heater.

Industrial feasibility

As concretely described in the above preferred embodiment, with an atomizer according to the invention, since it is possible to discharge atomized medicine in a uniformly dispersed state at all the times, it is possible to effectively display the effects of medicine without any loss.

What is claimed is:

1. An atomizer having a liquefied medicine atomizing means, a nozzle for discharging the atomized medicine outside and a feed means for sending out the medicine atomized by said atomizing means toward a nozzle side, and comprising an atomized medicine rectifying section which is provided between said medicine atomizing means and said nozzle, and being characterized in that:

said rectifying section has a guide cylindrical section disposed between said atomizing means and said nozzle with both the ends thereof open, a dome section having a roughly spherical inner face, which is disposed on the center axis of said guide cylindrical section so that the outer circumferential edge thereof is spaced from an inner circumferential face of said guide cylindrical section, and a slit hole provided in said guide cylindrical section for introducing an air flow from said feed means from a tangential direction of said dome section into said guide cylindrical section.

* * * * *